United States Patent [19]

Schwarz et al.

[11] 4,298,615

[45] Nov. 3, 1981

[54] SUBSTITUTED 2,3-DIHYDROBENZOFURYLMETHYL ESTERS, THEIR USE IN PEST CONTROL, AND PEST CONTROL AGENTS CONTAINING THESE COMPOUNDS

[75] Inventors: Gerd-Ulrich Schwarz, Mannheim; Karl Kiehs, Lampertheim; Walter Boell, Dannstadt-Schauernheim; Heinrich Adolphi, Limburgerhof, all of Fed. Rep. of Germany

[73] Assignee: BASF Aktiengesellschaft, Fed. Rep. of Germany

[21] Appl. No.: 172,526

[22] Filed: Jul. 28, 1980

[30] Foreign Application Priority Data

Aug. 4, 1979 [DE] Fed. Rep. of Germany ....... 2931672

[51] Int. Cl.[3] .................. A01N 43/08; C07D 307/82; C07D 307/79

[52] U.S. Cl. ............................... 424/285; 260/346.22

[58] Field of Search .................... 260/346.22; 424/285

[56] References Cited

U.S. PATENT DOCUMENTS 3,821,256 6/1974 Vollrath et al. ............... 260/346.22

FOREIGN PATENT DOCUMENTS 1440360 6/1976 United Kingdom .

*Primary Examiner*—Henry R. Jiles
*Assistant Examiner*—Bernard Dentz
*Attorney, Agent, or Firm*—Keil & Witherspoon

[57] ABSTRACT

Substituted 2,3-dihydrobenzofurylmethyl esters of the formula I

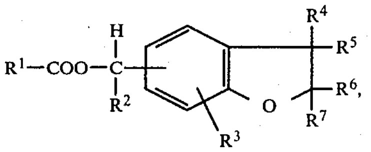

I where $R^1$ is 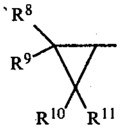 or 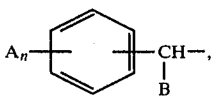

where $R^8$ is hydrogen or alkyl of up to 5 carbon atoms, $R^9$ is alkyl, haloalkenyl or haloalkynyl, each of up to 5 carbon atoms, $R^{10}$ is halogen or alkyl of up to 5 carbon atoms, $R^{11}$ is halogen or alkyl of up to 5 carbon atoms, A is halogen, alkyl, alkoxy, trihaloalkyl or trihaloalkoxy, each of up to 5 carbon atoms, cyano or nitro, B is alkyl, alkenyl or alkynyl, each of up to 4 carbon atoms, or an alicyclic radical of 3 to 7 carbon atoms and n is from 0 to 3, $R^2$ is hydrogen, cyano or alkyl, alkenyl or alkynyl, each of up to 5 carbon atoms, and $R^3$, $R^4$, $R^5$, $R^6$ and $R^7$ are identical or different and each is hydrogen, halogen or alkyl, alkenyl, alkynyl or alkoxy, each of up to 5 carbon atoms, and $R^9$ may also be alkenyl of up to 5 carbon atoms if $R^2$ is cyano or is alkyl, alkenyl or alkynyl, each of up to 5 carbon atoms.

The novel compounds are useful in pest control.

3 Claims, No Drawings

SUBSTITUTED 2,3-DIHYDROBENZOFURYLMETHYL ESTERS, THEIR USE IN PEST CONTROL, AND PEST CONTROL AGENTS CONTAINING THESE COMPOUNDS

The present invention relates to substituted 2,3-dihydrobenzofurylmethyl esters, a process for their preparation, pest control agents which contains these esters as active compounds, and a process for pest control using these active compounds.

The insecticidal activity of 2,2-dimethyl-3-(2',2'-dimethylvinyl)-cyclopropanecarboxylic acid esters in which the alcohol component is a substituted 2-methyl-2,3-dihydrobenzofuran radical has been disclosed in German Laid-Open Applications DOS 2,108,932 and DOS No. 2,255,581.

We have found that substituted 2,3-dihydrobenzofurylmethyl esters of the formula I

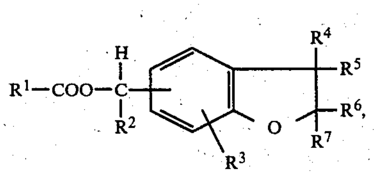

I where $R^1$ is 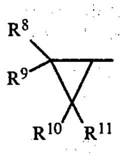 or 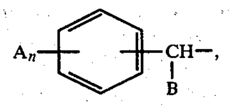, where $R_8$ is hydrogen or alkyl of up to 5 carbon atoms, $R^9$ is alkyl, haloalkenyl or haloalkynyl, each of up to 5 carbon atoms, $R^{10}$ is halogen or alkyl of up to 5 carbon atoms, $R^{11}$ is halogen or alkyl of up to 5 carbon atoms, A is halogen, alkyl, alkoxy, trihaloalkyl or trihaloalkoxy, each of up to 5 carbon atoms, cyano or nitro, B is alkyl, alkenyl or alkynyl, each of up to 4 carbon atoms, or an alicyclic radical of 3 to 7 carbon atoms and n is from 0 to 3, $R^2$ is hydrogen, cyano or alkyl, alkenyl or alkynyl, each of up to 5 carbon atoms, and $R^3$, $R^4$, $R^5$, $R^6$ and $R^7$ are identical or different and each is hydrogen, halogen or alkyl, alkenyl, alkynyl or alkoxy, each of up to 5 carbon atoms, and $R^9$ may also be alkenyl of up to 5 carbon atoms if $R^2$ is cyano or is alkyl, alkenyl or alkynyl, each of up to 5 carbon atoms, are very useful in the control of pests, especially of insects, mites and ticks.

In formula I, $R^1$ is 2,2-dialkylcyclopropyl substituted in the 3-position by alkyl, haloalkenyl or haloalkynyl, for example a 3-(2,2-dihalovinyl)-2,2-dimethylcyclopropyl radical, eg. 3-(2,2-dichlorovinyl)-2,2-dimethylcyclopropyl, 3-(2,2-dibromovinyl)-2,2-dimethylcyclopropyl or 3-(2,2-difluorovinyl)-2,2-dimethylcyclopropyl, or a 3-(2-haloethynyl)-2,2-dimethylcyclopropyl radical, eg. 3-(2-chloroethynyl)-2,2-dimethylcyclopropyl, or 3-(2-bromoethynyl)-2,2-dimethylcylopropyl, a 2,2,3,3-tetraalkylcyclopropyl radical, especially 2,2,3,3-tetramethylcyclopropyl, a 2,2-dihalo-3,3-dialkylcyclopropyl radical, especially 2,2-dichloro-3,3-dimethylcyclopropyl or 2,2-dibromo-3,3-dimethylcyclopropyl, or a 3-(2-haloalkenyl)-2,2-dimethylcyclopropyl radical, eg. 3-(2-chloroprop-1-enyl)-, 3-(2-bromo-prop-1-enyl)- or 3-(2-fluoroprop-1-enyl)-2,2-dimethylcyclopropyl, 3-(2-chlorobut-1-enyl)-, 3-(2-bromobut-1-enyl)- or 3-(2-fluorobut-1-enyl)-2,2-dimethylcyclopropyl, 3-(2-chloro-3-methyl-but-1-enyl)-, 3-(2-bromo-3-methyl-but-1-enyl)- or 3-(2-fluoro-3-methylbut-1-enyl)-2,2-dimethylcyclopropyl.

$R^1$ may also be a 2,2-dialkylcyclopropyl radical substituted in the 3-position by alkenyl, for example a 3-alkenyl-2,2-dimethylcyclopropyl radical, eg. 3-(2-methylprop-1-enyl)-2,2-dimethylcyclopropyl or 3-(2-methylbut-1-enyl)-2,2-dimethylcyclopropyl, if $R^2$ is cyano, alkyl, alkenyl or alkynyl.

$R^1$ may also be a radical of the formula

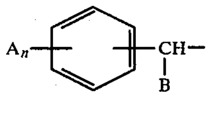

where n is from 0 to 3. Examples of substituents A are cyano, nitro, halogen, eg. fluorine, chlorine and bromine, unbranched and branched alkyl and alkoxy of up to 5 carbon atoms, eg. methyl, methoxy, ethyl, ethoxy, n-propyl, i-propyl, n-propoxy, i-propoxy, i-butyl, tert.-butyl, sec.-butoxy, n-butoxy, i-butoxy, n-pentyl, n-pentoxy, i-pentyl and i-pentoxy, and unbranched and branched trihaloalkyl and trihaloalkoxy of up to 3 carbon atoms, for example trihalomethyl and trihalomethoxy, eg. trifluoromethyl, trichloromethyl and trifluoromethoxy. If n is 2 or 3, the substituents A may be identical or different.

B in this formula may be unbranched or branched alkyl, alkenyl or alkynyl, each of up to 4 carbon atoms, eg. methyl, ethyl, isopropyl, tert.-butyl, isobutyl, allyl, isopropenyl, propargyl, or an alicyclic radical of 3 to 7 carbon atoms, eg. cyclopropyl or cyclohexyl.

Examples of unbranched and branched alkyl, alkenyl and alkynyl groups $R^2$ of up to 5 carbon atoms are methyl, ethyl, n-propyl, isopropyl, n-butyl, tert.-butyl, n-pentyl, isopentyl, vinyl, allyl, n-prop-1-enyl, isopropenyl, the n-butenyl radicals, 2-methyl-prop-1-enyl, the n-pentenyl radicals, the 1-methyl-n-propenyl radicals, the 1-methyl-n-butenyl radicals, ethynyl, isopropynyl, the n-propynyl radicals, the n-butynyl radicals, the n-pentynyl radicals, the 1-methyl-n-propynyl radicals and the 1-methyl-n-butynyl radicals.

Radicals $R^3$, $R^4$, $R^5$, $R^6$ and $R^7$ in formula I may be identical or different and may be halogen, eg. fluorine, chlorine or bromine, or unbranched or branched alkyl, alkoxy, alkenyl or alkynyl of up to 5 carbon atoms, eg. methyl, ethyl propyl, isopropyl, n-butyl, tert.-butyl, isobutyl, the isomeric pentyl radicals, methoxy, ethoxy, n-propoxy, isopropoxy, the isomeric butoxy or pentoxy radicals, vinyl, allyl, n-propenyl, isopropenyl, n-butenyl, the n-pentenyl radicals, the 1-methyl-n-propenyl radicals, the 1-methyl-n-butenyl radicals, ethynyl, n-propynyl, isopropynyl, n-butynyl, n-pentynyl, 1-methyl-propynyl and the 1-methyl-butynyl radicals.

Preferred compounds of the formula I are those in which $R^1$ is

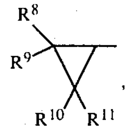

where $R^8$ is hydrogen, $R^9$ is haloalkenyl of the formula

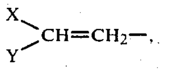

X and Y being identical or different halogen, and $R^{10}$ and $R^{11}$ are methyl, or where $R^8$ and $R^9$ are methyl and $R^{10}$ and $R^{11}$ are methyl, chlorine or bromine, and those in which $R^1$ is

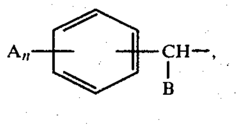

where A is fluorine, chlorine, bromine, methoxy or trifluoromethoxy, n is 1 and B is isopropyl. In these preferred compounds, $R^2$ is hydrogen, cyano, methyl, ethyl, n-propyl, isopropyl, vinyl, 2,2-dimethylvinyl, allyl or ethynyl, $R^3$ is hydrogen, chlorine or bromine and $R^4$, $R^5$, $R^6$ and $R^7$, which are identical or different, are hydrogen or methyl.

Specific examples of the novel 2,3-dihydrobenzofurylmethyl esters of the formula I are 2″,2″-dimethyl-2″,3″-dihydrobenzofuran-6″-yl-(α-vinyl)-methyl 2,2-dimethyl-3-(2′,2′-dichlorovinyl)-cyclopropanecarboxylate, 2″,2″-dimethyl-2″,3″-dihydrobenzofuran-6″-yl-(α-isopropyl)-methyl 2,2-dimethyl-3-(2′,2′-dichlorovinyl)-cyclopropanecarboxylate, 2″,2″-dimethyl-2″,3″-dihydrobenzofuran-6″-yl-(α-cyano)-methyl 2,2-dimethyl-3-(2′,2′-dichlorovinyl)-cyclopropanecarboxylate, 2″,2″-dimethyl-2″,3″-dihydrobenzofuran-6″-yl-methyl 2,2-dimethyl-3-(2′,2′-dichlorovinyl)cyclopropanecarboxylate, 2″,2″-dimethyl-2″,3″-dihydrobenzofuran-6″-yl-methyl 2-(4′-chlorophenyl)-isovalerate, 2″,2″-dimethyl-2″,3″-dihydrobenzofuran-6″-yl-(α-allyl)-methyl 2,2-dimethyl-3-(2′,2′-dichlorovinyl)-cyclopropanecarboxylate, 2″,2″-dimethyl-2″,3″-dihydrobenzofuran-6″-yl-(α-ethynyl)-methyl 2,2-dimethyl-3-(2′,2′-dichlorovinyl)-cyclopropanecarboxylate, 2″,2″-dimethyl-2″,3″-dihydrobenzofuran-6″-yl-methyl 2,2-dimethyl-3-(2′,2′-difluorovinyl)-cyclopropanecarboxylate, 2″,2″-dimethyl-2″,3″-dihydrobenzofuran-6″-yl-methyl 2,2-dimethyl-3-(2′,2′-dibromovinyl)-cyclopropanecarboxylate, 2″,2″-dimethyl-2″,3″-dihydrobenzofuran-6″-yl-(α-vinyl)-methyl 2,2-dimethyl-3-(2′,2′-dibromovinyl)-cyclopropanecarboxylate, 2″,2″-dimethyl-2″,3″-dihydrobenzofuran-6″-yl-(α-allyl)-methyl 2,2-dimethyl-3-(2′,2′-dibromovinyl)-cyclopropanecarboxylate, 2″,2″-dimethyl-2″,3″-dihydrobenzofuran-6″-yl-(α-ethynyl)-methyl 2,2-dimethyl-3-(2′,2′-dibromovinyl)-cyclopropanecarboxylate, 2″,2″-dimethyl-2″,3″-dihydrobenzofuran-6″-yl-(α-cyano)-methyl 2,2-dimethyl-3-(2′,2′-dibromovinyl)-cyclopropanecarboxylate, 2″,2″-dimethyl-2″,3″-dihydrobenzofuran-6″-yl-(α-isopropyl)-methyl 2,2-dimethyl-3-(2′,2′-dibromovinyl)-cyclopropanecarboxylate, 2″,2″-dimethyl-2″,3″-dihydrobenzofuran-6″-yl-(α-vinyl)-methyl 2-(4′-chlorophenyl)-isovalerate, 2″,2″-dimethyl-2″,3″-dihydrobenzofuran-6″-yl-(α-ethynyl)-methyl 2-(4′-chlorophenyl)-isovalerate, 2″,2″-dimethyl-2″,3″-dihydrobenzofuran-6″-yl-(α-cyano)-methyl 2-(4′-chlorophenyl)-isovalerate, 2″,2″-dimethyl-2″,3″-dihydrobenzofuran-6″-yl-(α-isopropyl)-methyl 2-(4′-chlorophenyl)-isovalerate, 2″,2″-dimethyl-2″,3″-dibrohydrofuran-6″-yl-(α-allyl)-methyl 2-(4′-chlorophenyl)-isovalerate, 2″,2″-dimethyl-2″,3″-dihydrobenzofuran-6″-yl-methyl 2,2,3,3-tetramethyl-cyclopropanecarboxylate, 2″,2″-dimethyl-2″,3″-dihydrobenzofuran-6″-yl-(α-vinyl)-methyl 2,2,3,3-tetramethyl-cyclopropanecarboxylate, 2″,2″-dimethyl-2″,3″-dihydrobenzofuran-6″-yl-(α-ethynyl)-methyl 2,2,3,3-tetramethyl-cyclopropanecarboxylate, 2″,2″-dimethyl-2″,3″-dihydrobenzofuran-6″-yl-(α-isopropyl)-methyl 2,2,3,3-tetramethyl-cyclopropanecarboxylate, 2″,2″-dimethyl-2″,3″-dihydrobenzofuran-6″-yl-(α-cyano)-methyl 2,2,3,3-tetramethyl-cyclopropanecarboxylate, 2″,2″-dimethyl-2″,3″-dihydrobenzofuran-6″-yl-(α-allyl)-methyl 2,2,3,3-tetramethyl-cyclopropanecarboxylate, 2″,2″-dimethyl-2″,3″-dihydrobenzofuran-6″-yl-methyl 2,2-dichloro-3,3-dimethylcyclopropanecarboxylate, 2″,2″-dimethyl-2″,3″-dihydrobenzofuran-6″-yl-(α-vinyl)-methyl 2,2-dichloro-3,3-dimethyl-cyclopropanecarboxylate, 2″,2″-dimethyl-2″,3″-dihydrobenzofuran-6″-yl-(α-ethynyl)-methyl 2,2-dichloro-3,3-dimethyl-cyclopropanecarboxylate, 2″,2″-dimethyl-2″,3″-dihydrobenzofuran-6″-yl-(α-isopropyl)-methyl 2,2-dichloro-3,3-dimethyl-cyclopropanecarboxylate, 2″,2″-dimethyl-2″,3″-dihydrobenzofuran-6″-yl-(α-cyano)-methyl 2,2-dichloro-3,3-dimethyl-cyclopropanecarboxylate, 2″,2″-dimethyl-2″,3″-dihydrobenzofuran-6″-yl-(α-allyl)-methyl 2,2-dichloro-3,3-dimethyl-cyclopropanecarboxylate, 2″,2″-dimethyl-2″,3″-dihydrobenzofuran-6″-yl-(α-vinyl)-methyl 2,2-dimethyl-3-(2′,2′-dimethylvinyl)-cyclopropanecarboxylate, 2″,2″-dimethyl-2″,3″-dihydrobenzofuran-6″-yl-(α-ethynyl)-methyl 2,2-dimethyl-3-(2′,2′-dimethylvinyl)-cyclopropanecarboxylate, 2″,2″-dimethyl-2″,3″-dihydrobenzofuran-6″-yl-(α-isopropyl)-methyl 2,2-dimethyl-3-(2′,2′-dimethylvinyl)-cyclopropanecarboxylate, 2″,2″-dimethyl-2″,3″-dihydrobenzofuran-6″-yl-(α-cyano)-methyl 2,2-dimethyl-3-(2′,2′-dimethylvinyl)-cyclopropanecarboxylate, 2″,2″-dimethyl-2″,3″-dihydrobenzofuran-6″-yl-(α-allyl)-methyl 2,2-dimethyl-3-(2′,2′-dimethylvinyl)-cyclopropanecarboxylate, 2″,2″-dimethyl-2″,3″-dihydrobenzofuran-4″-yl-(α-allyl)-methyl 2,2-dimethyl-3-(2′,2′-dichlorovinyl)-cyclopropanecarboxylate, 2″,2″-dimethyl-2″,3″-dihydrobenzofuran-4″-yl-(α-ethynyl)-methyl 2,2-dimethyl-3-(2′,2′-dichlorovinyl)-cyclopropanecarboxylate, 2″,2″-dimethyl-2″,3″-dihydrobenzofuran-4″-yl-methyl 2,2-dimethyl-3-(2′,2′-difluorovinyl)-cyclopropanecarboxylate, 2″,2″-dimethyl-2″,3″-dihydrobenzofuran-4″-yl-methyl 2,2-dimethyl-3-(2′,2′-dibromovinyl)-cyclopropanecarboxylate, 2″,2″-dimethyl-2″,3″-dihydrobenzofuran-4″-yl-(α-vinyl)-methyl 2,2-dimethyl-3-(2′,2′-dibromovinyl)-cyclopropanecarboxylate, 2″,2″-dimethyl-2″,3″-dihydrobenzofuran-4″-yl-(α-allyl)-methyl 2,2-dimethyl-3-(2′,2′-dibromovinyl)-cyclopropanecarboxylate, 2″,2″-dimethyl-2″,3″-dihydrobenzofuran-4″-yl-(α-ethynyl)-methyl 2,2-dimethyl-3-(2′,2′-dibromovinyl)-cyclopropanedarboxylate, 2″,2″-dimethyl-2″,3″-dihydrobenzofuran-4″-yl-(α-cyano)-methyl 2,2-dimethyl-3-(2′,2′-dibromovinyl)-cyclopropanecarboxylate, 2″,2″-dimethyl-2″,3″-dihydrobenzofuran-4″-yl-(α-isopropyl)-methyl 2,2-dimethyl-3-(2′,2′-dibromovinyl)-cyclopropanecarboxylate, 2″,2″-dimethyl-2″,3″-dihydrobenzofuran- 4″-yl-(α-vinyl)-methyl 2-(4′-chlorophenyl)-isovalerate, 2″,2″-dimethyl-2″,3″-dihydrobenzofuran-4″-yl-(α-ethynyl)-methyl 2-(4′-chlorophenyl)-isovalerate, 2″,2″-dimethyl-2″,3″-dihydrobenzofuran-4″-yl-(α-cyano)-methyl 2-(4′-chlorophenyl)-isovalerate, 2″,2″-dimethyl-2″,3″-dihydrobenzofuran-4″-yl-(α-isopropyl)-methyl 2-(4′-chlorophenyl)-isovalerate, 2″,2″-dimethyl-2″,3″-dihydrobenzofuran-4″-yl-(α-allyl)-methyl 2-(4′-chlorophenyl)-isovalerate, 2″,3″-dimethyl-2″,3″-dihydrobenzofuran-6″-yl-(α-allyl)-methyl 2,2-dimethyl-3-(2′,2′-dichlorovinyl)-cyclopropanecarboxylate, 2″,3″-dimethyl-2″,3″-dihydrobenzofuran-6″-yl-(α-ethynyl)-methyl 2,2-dimethyl-3-(2′,2′-dichlorovinyl)-cyclopropanecarboxylate, 2″,3″-dimethyl-2″,3″-dihydrobenzofuran-6″-yl-methyl 2,2-dimethyl-3-(2′,2′-difluorovinyl)-cyclopropanecarboxylate, 2″,3″-dimethyl-2″,3″-dihydrobenzofuran-6″-yl-methyl 2,2-dimethyl-3-(2′,2′-dibromovinyl)-cyclopropanecarboxylate, 2″,3″-dimethyl-2″,3″-dihydrobenzofuran-6″-yl-(α-vinyl)-methyl 2,2-dimethyl-3-(2′,2′-dibromovinyl)-cyclopropanecarboxylate, 2″,3″-dihydrobenzofuran-6″-yl-(α-allyl)-methyl 2,2-dimethyl-3-(2′,2′-dibromovinyl)-cyclopropanecarboxylate, 2″,3″-dihydrobenzofuran-6″-yl-(α-ethynyl)-methyl 2,2-dimethyl-3-(2′,2′-dibromovinyl)-cyclopropanecarboxylate, 2″,3″-dihydrobenzofuran-6″-yl-(α-cyano)-methyl 2,2-dimethyl-3-(2′,2′-dibromovinyl)-cyclopropanecarboxylate, 2″,3″-dihydrobenzofuran-6″-yl-(α-isopropyl)-methyl 2,2-dimethyl-3-(2′,2′-dibromovinyl)-cyclopropanecarboxylate, 2″,3″-dimethyl-2″,3″-dihydrobenzofuran-6″-yl-(α-vinyl)-methyl 2-(4′-chlorophenyl)-isovalerate, 2″,3″-dimethyl-2″,3″-dihydrobenzofuran-6″-yl-(α-ethynyl)-methyl 2-(4′-chlorophenyl)-isovalerate, 2″,3″-dimethyl-2″,3″-dihydrobenzofuran-6″-yl-(α-cyano)-methyl 2-(4′-chlorophenyl)-isovalerate, 2″,3″-dimethyl-2″,3″-dihydrobenzofuran-6″-yl-(α-isopropyl)-methyl 2-(4′-chlorophenyl)-isovalerate and 2″,3″-dimethyl-2″,3″-dihydrobenzofuran-6″-yl-(α-allyl)-methyl -2-(4′-chlorophenyl)-isovalerate.

Of course of the nomenclature of the esters includes all the possible stereoisomers.

Further, we have found that the 2,3-dihydrobenzofurylmethyl esters of the formula I are obtained by reacting an acid halide of the formula II $R^1$—CO—Hal II, where $R^1$ has the above meanings and Hal is halogen, especially chlorine, with a compound of the formula III

III

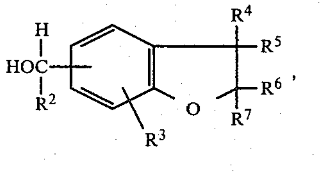

where $R^2$, $R^3$, $R^4$, $R^5$, $R^6$ and $R^7$ have the above meanings, in the presence of an acid-binding agent.

The novel esters of the formula I may also be prepared by reacting an acid of the formula IV $R^1$—COOH IV, where $R^1$ has the above meanings, with a halide of the formula V

V

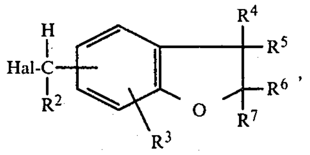

where $R^2$, $R^3$, $R^4$, $R^5$, $R^6$ and $R^7$ have the above meanings and Hal is halogen, especially chlorine, in the presence of an acid-binding agent.

Further possible methods of synthesis include the reaction of an acid of the formula IV with a compound of the formula III in the presence of a water-binding agent, and the reaction of an alkyl ester of the formula VI $R^1$—COOR VI, where $R^1$ has the above meanings and R is unbranched or branched alkyl of 1 to 5 carbon atoms, with a compound of the formula III in the presence of a conventional trans-esterification catalyst.

The various methods of synthesis can be represented by the following equations:

$R^1$—CO—Hal + (a)

II

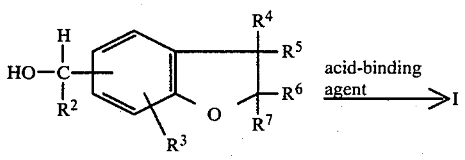

III $R^1$—COOH + (b)

IV

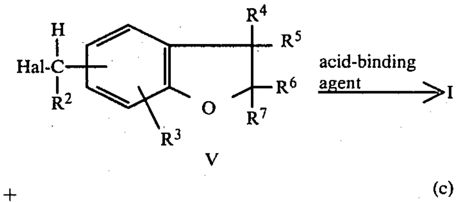

V $R^1$—COOH + (c)

IV

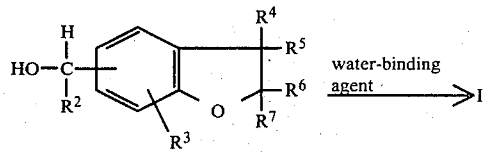

III $R^1$—COOR + (d)

VI

-continued

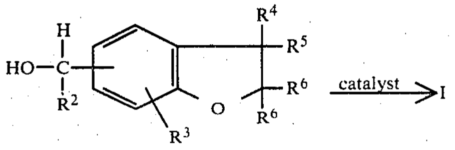

III

Suitable acid-binding agents to be used in syntheses (a) and (b) are organic bases, for example tertiary amines, eg. triethylamine, trimethylamine, dimethylaniline, dimethylbenzylamine, 4-dimethylaminopyridine, 4pyrrolidinopyridine or pyridine, and inorganic bases, for example hydroxides, oxides, bicarbonates or carbonates of alkali metals and of alkaline earth metals, eg. sodium hydroxide, potassium hydroxide, calcium hydroxide, calcium bicarbonate and potassium carbonate, and alcoholates and hydrides of the alkali metals, eg. sodium hydride and potassium t.-butylate. At least one mole of acid-binding agent is employed per mole of compound of the formula II or V.

Examples of suitable water-binding agents for the reaction according to equation (c) are dicyclohexylcarbodiimide, inorganic acids, eg. sulfuric acid and phosphoric acid, acidic ion exchangers and p-toluenesulfonic acid. At least 0.02, advantageously from 0.05 to 0.4, mole of water-binding agent is used per mole of reactant III or IV.

Suitable catalysts for the reaction according to equation (d) are alkali metal hydrides and alcoholates, eg. sodium hydride, sodium ethylate, and triphenyl-sodium. Alcoholates of elements of group IV b of the periodic table, eg. titanium tetramethylate and titanium tetraethylate, may also be used. Advantageously, from 0.02 to 0.4 mole of catalyst is added per mole of ester of the formula VI.

Each of the processes (a) to (d) may be carried out at from −10° to +150° C., under atmospheric or superatmospheric pressure, batchwise or continuously.

Preferably, the processes are carried out with equimolar ratios of the reactants of the formulae II and III, IV and V, IV and III or VI and III. Using an excess of one or other component offers no substantial advantages. The reaction is virtually quantitative.

Processes (a) to (d) are advantageously carried out in the presence of a suitable solvent or diluent. Virtually all inert organic solvents may be used for this purpose. They include acyclic and cyclic ethers, eg. diethyl ether, tetrahydrofuran and dioxane, alkylated aliphatic and alicyclic carboxylic acid amides, eg. dimethylformamide and N-methylpyrrolidone, aliphatic and aromatic hydrocarbons or chlorohydrocarbons, eg. toluene, xylenes, chloroform, n-hexane, cyclohexane and chlorobenzene, ketones, eg. acetone and methyl ethyl ketone, nitriles, eg. acetonitrile, and also dimethylsulfoxide and hexamethylphosphorotriamide. Mixtures of these solvents may also be used.

The process according to equation (a) may also be carried out in aqueous solution. Processes (a) and (b) may furthermore be carried out as two-phase reactions, in which case the water-insoluble organic phase may be, for example, an ether, aliphatic or aromatic hydrocarbon or chlorohydrocarbon, especially toluene or chloroform, or methyl ethyl ketone.

If the starting materials used for the preparation of the esters of the formula I are not individual optically active isomers or cis-/trans-isomers, the end products obtained are mixtures of various optically active isomers or cis/trans-isomers. These isomer mixtures may be separated into the individual isomers by conventional methods. For the purposes of the invention, esters of the formula I includes both the pure isomers and their mixtures.

Some of the starting compounds of the formula II are known (British Pat. No. 1,446,304 and U.S. Pat. No. 3,981,903); compounds not previously known may be prepared by analogy with conventional processes. Again, some of the compounds of the formula III are known (German Laid-Open Applications DOS No. 2,108,932 and DOS No. 2,255,581); where they are not previously known they can be prepared by conventional processes, for example by reacting an aldehyde with a metal-organyl or by forming an adduct of an alkyne with an aldehyde, and then partially hydrogenating the product (Houben-Weyl, Methoden der organischen Chemie, Volume V/lb, pages 775–790, Georg Thieme-Verlag, Stuttgart, 1972). Compounds of the formulae IV, V and VI are also known or obtainable by conventional processes (U.S. Pat. Nos. 3,979,519 and 3,981,903, Belgian Pat. No. 801,946 and German Laid-Open Applications DOS No. 2,365,555 and DOS No. 2,231,312).

The Examples which follow illustrate the preparation of the novel esters of the formula I.

EXAMPLE 1

73 ml of a 1.6-molar solution of vinyl-magnesium chloride in tetrahydrofuran are introduced into 200 ml of absolute tetrahydrofuran at 0° C. 17.6 g of 2,2-dimethyl-2,3-dihydrobenzofuran-6-aldehyde in 100 ml of absolute tetrahydrofuran are then added dropwise whilst stirring, in the absence of moisture. Thereafter, the reaction mixture is stirred for 3 hours at 25° C., after which it is cautiously decomposed with a cold saturated ammonium chloride solution and a few milliliters of 10% strength hydrochloric acid, sufficient to dissolve the precipitate. The mixture is extracted three times by shaking with ether and the combined ether extracts are washed with sodium bisulfite solution, sodium bicarbonate solution and water, dried over sodium sulfate and concentrated under reduced pressure.

17.7 g of 2,2-dimethyl-2,3-dihydrobenzofuran-6-yl-(α-vinyl)-carbinol are obtained in the form of a yellowish oil which is sufficiently pure for the subsequent reaction. (Yield 87% of theory).

8.8 g of 2,2-dimethyl-2,3-dihydrobenzofuran-6-yl-(α-vinyl)-carbinol are introduced into 100 ml of absolute ether and 7 g of pyridine at 0°–10° C. 9 g of chrysanthemic acid chloride in 20 ml of absolute ether are slowly added dropwise to this solution. The mixture is stirred overnight at 25° C. and the precipitate is then filtered off. The ether phase is washed with 2 N hydrochloric acid, 2 N sodium bicarbonate solution and water, dried over sodium sulfate and concentrated.

15.4 g of 2,2-dimethyl-2,3-dihydrobenzofuran-6-yl-(α-vinyl)-methyl 3-(2,2-dimethylvinyl)-2,2-dimethylcyclopropanecarboxylate are obtained in the form of a yellowish oil which is purified on a silica gel column, with toluene as the eluant.

Calculated: C 77.93; H 8.53; O 13.54. Found: C 77.8 H 8.6; O 13.7.

$n_D^{21} = 1.5236$

EXAMPLE 2

18.7 g of 2-bromopropane in 30 ml of absolute tetrahydrofuran are added dropwise to 3.6 g of Mg filings in 15 ml of absolute tetrahydrofuran. The mixture is stirred under reflux for 1 hour and is then cooled to 5°–10° C. At this temperature, 23 g of 2,2-dimethyl-2,3-dihydrobenzofuran-6-aldehyde in 100 ml of absolute tetrahydrofuran are added dropwise. The reaction mixture is stirred overnight and is then cautiously decomposed with a cold saturated ammonium chloride solution and a few milliliters of 10% strength hydrochloric acid, sufficient to dissolve the precipitate. The mixture is then extracted three times by shaking with ether and the combined ether extracts are washed with sodium bisulfate solution, sodium bicarbonate solution and water, dried over sodium sulfate and concentrated under reduced pressure. 19.5 g of 2,2-dimethyl-2,3-dihydrobenzofuran-6-yl-(α-isopropyl)-carbinol are obtained in the form of a yellowish oil, which is sufficiently pure for the subsequent reactions. (Yield 68%).

9.5 g of 2,2-dimethyl-2,3-dihydrobenzofuran-6-yl-(α-isopropyl)-carbinol in 100 ml of absolute ether and 7 g of pyridine are introduced into the reaction vessel at 0°–10° C. 9 g of chrysanthemic acid chloride are added dropwise to this solution. The batch is stirred overnight and is then worked up similarly to Example 1. 15 g of 2,2-dimethyl-2,3-dihydrobenzofuran-6-yl-(α-isopropyl)-methyl 3-(2,2-dimethylvinyl)-2,2-dimethylcyclopanecarboxylate are obtained in the form of a yellowish oil which is purified on a silica column, with toluene as the eluant.

Calculated: C 77.80; H, 9.25; O 12.95. Found: C 77.3; H 9.0; O 13.3.

$n_D^{21}=1.5165$

EXAMPLE 3

A two-phase reaction is carried out by stirring 8.8 g of 2,2-dimethyl-2,3-dihydrobenzofuran-6-aldehyde in 150 ml of ether, 3.9 g of potassium cyanide in 50 ml of water and 0.5 g of triethylbenzylammonium chloride vigorously at 5°–10° C. After one hour, 12.7 g of 2-(4-chlorophenyl)-isovaleryl chloride are slowly added dropwise to this reaction mixture. The batch is stirred overnight at 25° C. The organic phase is then separated off and the aqueous phase is twice extracted by shaking with ether. The combined organic phases are washed with sodium bisulfate solution, sodium bicarbonate solution and water, dried over sodium sulfate and concentrated under reduced pressure.

17.8 g of 2,2-dimethyl-2,3-dihydrobenzofuran-6-yl-(α-cyano)-methyl 1-4-chlorophenyl)-isovalerate are obtained in the form of a yellowish oil which is purified on a silica gel column, with toluene as the eluant (Yield: 81% of theory).

Calculated: C 69.43; H 6.08; O 12.06; N 3.52; Cl 8.91. Found: C 69.4; H 6.3; O 11.6; N 3.3; Cl 8.6.

$n_D^{21}=1.5388$

EXAMPLE 4

13 g of 2,2-dimethyl-3-(2-bromoethynyl)-cyclopropanecarboxylic acid in 100 ml of toluene, 10.7 g of 2,2-dimethyl-2,3-dihydrobenzofuran-6-yl-carbinol and 1 g of p-toluenesulfonic acid are refluxed for 6 hours under a water separator. After cooling, the mixture is washed with sodium bicarbonate solution and with water and the organic phase is dried over sodium sulfate and concentrated under reduced pressure.

15 g of 2,2-dimethyl-2,3-dihydrobenzofuran-6-yl-methyl 3-(2′-bromoethynyl)-2,2-dimethylcyclopropanecarboxylate are obtained in the form of a yellowish oil which is purified on a silica gel column, with toluene as the eluant; yield: 66% of theory.

($^1$H-NMR, 80 MHz, $CDCl_3$, δ in ppm: 3H (m) 7.05–6.67; 2H (s) 5.01; 2H (s) 2.98; 2H (q) 1.93 and 1.74, $J_{AB}$ 5.6 Hz; 6H (s) 1.46; 3H (s) 1.27; 3H (s) 1.21).

The following compounds may be prepared similarly:

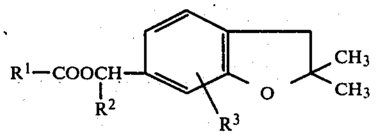

| No. | $R^1$ | $R^2$ | $R^3$ | $n_D$ |
|---|---|---|---|---|
| 1 | 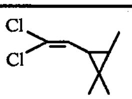 | H | H | 1.5362 (23° C.) |
| 2 | 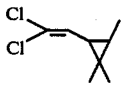 | CN | H | 1.5330 (21° C.) |
| 3 | 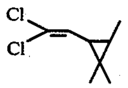 | $CH{=}CH_2$ | H | 1.543 (21° C.) |
| 4 | 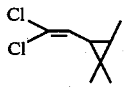 | i-$C_3H_7$ | H | 1.5337 (21° C.) |
| 5 | 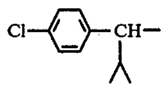 | H | H | 1.5425 (23° C.) |
| 6 | 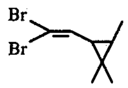 | H | H | 1.5552 (23° C.) |
| 7 | 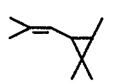 | CN | H | 1.5190 (21° C.) |

| No. | $R^1$ | $R^2$ | $R^3$ | $n_D$/Analysis |
|---|---|---|---|---|
| 8 | 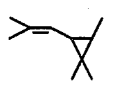 | i-$C_3H_7$ | H | 1.5165 (21° C.) |
| 9 | 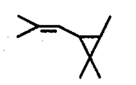 | $CH{=}CH_2$ | H | 1.5236 (21° C.) |
| 10 | 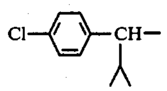 | CN | H | 1.5388 (21° C.) |
| 11 | 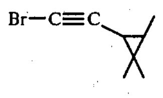 | H | H | (cf. Ex. 4) |
| 12 | 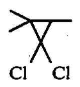 | H | H | 1.5300 (24° C.) |
| 13 | 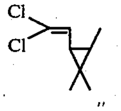 | $CH_3$ | H | 1.5345 (23° C.) |
| 14 | " | $C_2H_5$ | H | 1.5315 (23° C.) |
| 15 | " | n-$C_4H_9$ | H | 1.5240 (24° C.) |

-continued

| | | | | |
|---|---|---|---|---|
| 16 | 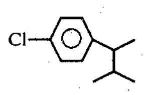 | $CH_3$ | H | 1.5375 (23° C.) |
| 17 | 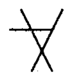 | H | H | calc. C 75.34<br>H 8.67<br>found C 75.2<br>H 8.5 |

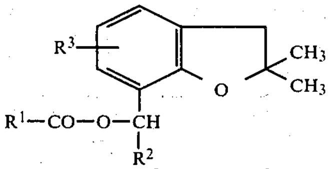

| No. | $R^1$ | $R^2$ | $R^3$ | $n_D$ |
|---|---|---|---|---|
| 18 | 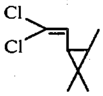 | H | 5-Cl | 1.5446 (24° C.) |
| 19 | 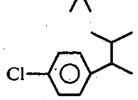 | H | 5-Cl | 1.5482 (23° C.) |
| 20 | 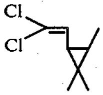 | H | H | 1.5373 (24° C.) |
| 21 | 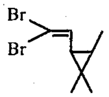 | H | H | 1.5540 (24° C.) |
| 22 | 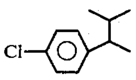 | H | H | 1.5430 (24° C.) |
| 23 | 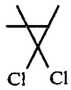 | H | H | 1.5310 (23° C.) |
| 24 | 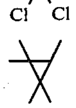 | H | H | 1.5135 (23° C.) |
| 25 | 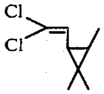 | CN | H | 1.5391 (23° C.) |
| 26 | " | $CH{=}CH_2$ | H | 1.5379 (23° C.) |
| 27 | " | 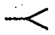 | H | 1.5283 (23° C.) |
| 28 | " | n-$C_4H_9$ | H | 1.5236 (23° C.) |
| 29 | 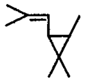 | CN | H | 1.5213 (23° C.) |

The esters according to the invention are suitable for effectively combating pests from the classes of insects, mites and ticks.

Examples of injurious insects from the Lepidoptera order are *Hepialus humuli, Oncopera fasciculata, Oxycanus cerrinatus, Tinea cloacella, Tinea pellionella, Tineola bisselliella, Lyonetia clerkella, Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineathus, Otiorrhynchus sulcatus, Otiorrhynchus ovatus, Hylobies abietis, Byctiscus betulae, Anthonomus pomorum, Anthonomus gradis, Ceuthorrphynchus assimilis, Ceuthorrhynchus napi, Sitophilus granaria, Anisandrus dispar, Ips typographus,* and *Blastophagus piniperda;* examples from the Diptera order are *Lycorca pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Tipula oleracea, Musca domestica, Fannia canicularis, Muscina stabulans, Glossina morsitans, Oestrus ocis, Chrysomya macellaria, Chrysomya hominivorax, Lucilia cuprina, Lucilia sericata,* and *Hypoderma lineata;* examples from the Hymenoptera order are *Athalia rosae, Haplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes* and *Termes natalensis;* examples from the Orthoptera order are *Forficula auricularia, Acheta domestica, Gryllotalpa gryllotalpa, Tachnycines asynamorus, Locusta migratoria, Stauronotus macroccanus, Schistocerca peregrina, Nomadacris septemfasciata, Melanoplus spretus, Melanoplus femurrubrum, Blatta orientalis, Blattella germanica, Periplaneta americana,* and *Blabera gigantea.*

Examples of mites and ticks (Acarina) belonging to the Arachnida class are *Tetranychus telarius, Tetrany-*

*chus atlanticus, Tetranychus pacificus, Paratetranhychus pilosus, Bryobia praetiosa, Ixodes ricinus, Ornithodorus moubata, Ablyomma americanum, Dermacentor silvarum,* and *Boophilus microplus.*

The compounds according to the invention may be successfully employed as pesticides for protecting crops and in the hygiene, stores protection and veterinary sectors.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredients are applied in the form of these formulations or of ready-to-use preparations made therefrom.

The amount of active ingredient in the ready-to-use preparations may vary within a wide range; it is generally from 0.0001 to 10%, preferably from 0.01 to 1%.

The active ingredients may also be successfully used in the ultra-low volume method, where it is possible to apply formulations containing more than 95 wt% of active ingredient, or even the 100% active ingredient.

Examples of formulations are given below:

I. 3 parts by weight of 2″,2″-dimethyl-2″,3″-dihydrobenzofuran-6″-yl-α-vinyl)-methyl 2,2-dimethyl-3-(2′,2′-dichlorovinyl)-cyclopropanecarboxylate is intimately mixed with 97 parts by weight of particulate kaolin. A dust is obtained containing 3% by weight of the active ingredient.

II. 30 parts by weight of 2″,2″-dimethyl-2″,3″-dihydrobenzofuran-6″-yl-methyl 2,2-dimethyl-3-(2′,2′-dichlorovinyl)-cyclopropanecarboxylate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of 2″,2″-dimethyl-2″,3″-dihydrobenzofuran-6″-yl-(α-isopropyl)-methyl 2,2-dimethyl-3-(2′,2′-dichlorovinyl)-cyclopropanecarboxylate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of 2″,2″-dimethyl-2″,3″-dihydrobenzofuran-6″-yl-methyl 3-(2′-bromoethynyl)-2,2-dimethylcyclopropanecarboxylate is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

There may be added to the individual active ingredients or mixtures thereof (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows:

1,2-dibromo-3-chloropropane, 1,3-dichloropropene, 1,3-dichloropropene +1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethylphosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phen-oxybenzyl-α-isopropyl-4-chlorophenylacetate.

Compounds of the formula I are particularly advantageously combined with substances having a synergistic or intensifying effect on pyrethroids. Examples of such compounds are piperonyl butoxide, propynyl ethers, propynyl oximes, propynyl carbamates and propynyl phosphonates, 2-(3,4-methylenedioxyphenoxy)-3,6,9-trioxaundecane, S,S,S-tributylphosphorotrithioates, 1,2-methylenedioxy-4-(2-octylsulfonyl)-propyl)-benzene, 1-n-dodecylimidazole, 1-(1,5,9-trimethyldecyl)-imidazole, 1-[2-chloro-2(4-fluorophenyl)-ethyl]-1,2,4-triazole, 1-(2-phenylethyl)-1,2,4-triazole, 1-(2-chloro-2-phenylethyl)-1,2,4-triazole and 1-(3-phenyl-n-propyl)-1,2,4-triazole.

The following examples demonstrate the biological action of the new esters. The comparison compound is 2,2-dimethyl-2,3-dihydrobenzofuran-6-yl-methyl 2,2-dimethyl-3-(2',2'-dimethylvinyl)-cyclopropanecarboxylate (German Laid-Open Application DOS 2,108,932). The other active ingredients are numbered as in the table above.

EXAMPLE A

Continuous contact action on houseflies (*Musca domestica*)

Both covers and bottoms of Petri dishes 10 cm in diameter are lined with a total per dish of 2 ml of acetonic solutions of the active ingredients. After the solvent has evaporated (about 30 mins.), 10 flies are introduced into each dish. The kill rate is determined after 4 hours.

| Active ingredient no. | Amount of active ingredient per dish (mg) | Kill rate (%) |
|---|---|---|
| 1 | 0.052 | 100 |
| 2 | 2.0 | 100 |

-continued

| Active ingredient no. | Amount of active ingredient per dish (mg) | Kill rate (%) |
|---|---|---|
| 3 | 0.2 | 100 |
| 4 | 0.01 | 100 |
| 5 | 0.2 | 100 |
| 6 | 0.005 | 100 |
| 8 | 0.2 | 100 |
| 9 | 0.2 | 100 |
| 11 | 0.2 | 100 |

EXAMPLE B

Contact action on houseflies (*Musca domestica*)

1 μl of the active ingredients dissolved in acetone is administered by means of a microsyringe to the ventral abdomen of 4-day old imagoes under slight $CO_2$ narcosis.

20 animals treated in the same way are then placed in a plastic bag having a volume of approx. 50 ml. After 4 hours, the animals in supine position are counted and the $LD_{50}$ is worked out by means of a graph.

| Active ingredient no. | $LD_{50}$ |
|---|---|
| 1 | 0.017/μg/fly |
| 4 | 0.03/μg/fly |
| 6 | 0.022/μg/fly |
| Comparison compound | 0.12/μg/fly |

EXAMPLE C

Contact action and effect of ingested food on caterpillars of the diamondback moth (*Plutella maculipennis*)

Leaves of young cabbage plants are dipped for 3 seconds in aqueous emulsions of the active ingredients and, after excess liquid has been briefly allowed to drip off, placed on a moist filter paper in a Petri dish. 10 caterpillars of the 4th stage are then placed on each leaf. The action is assessed after 48 hours.

| Active ingredient | Active ingredient concentration in emulsion (wt%) | Kill rate (%) |
|---|---|---|
| 1 | 0.005 | 100 |
| | 0.002 | approx. 80 |
| 3 | 0.02 | 100 |
| 4 | 0.02 | 100 |
| | 0.01 | approx. 80 |
| 5 | 0.05 | approx. 80 |
| 6 | 0.004 | 100 |
| 8 | 0.02 | approx. 80 |
| 9 | 0.1 | 100 |
| 11 | 0.05 | approx. 80 |

EXAMPLE D

Contact action on mosquito larvae (*Aedes aegypti*)

The active ingredient formulations are added to 200 ml of tapwater, and 30 to 40 mosquito larvae in the 4th larval stage are then introduced. The temperature is kept at 20° C. The action is assessed after 25 hours.

| Active ingredient no. | Concentration of active ingredient in formulation (ppm) | Kill rate (%) |
|---|---|---|
| 1 | 0.01 | 100 |

-continued

| Active ingredient no. | Concentration of active ingredient in formulation (ppm) | Kill rate (%) |
|---|---|---|
| 4 | 0.02 | 100 |
| 6 | 0.02 | 100 |
| Comparison compound | 0.04 | approx. 80 |

EXAMPLE E

Contact action on ticks (*Ornithodorus moubata*)

Ticks in the 3rd larval stage are placed in paper bags and dipped for 3 seconds in the emulsion under investigation. The bags are then suspended. The action on the ticks is assessed after 48 hours.

| Active ingredient no. | Concentration of active ingredient in emulsion (ppm) | Kill rate (%) |
|---|---|---|
| 1 | 5 | 100 |
| 3 | 20 | 100 |
| 4 | 20 | 100 |
| 5 | 50 | 100 |
| 6 | 20 | 100 |

We claim:

1. A substituted 2,3-dihydrobenzofurylmethyl ester of the formula

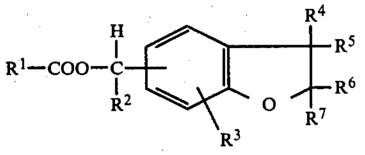

where $R^1$ is 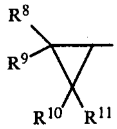 or 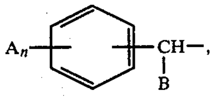, where $R^8$ is hydrogen or alkyl of up to 5 carbon atoms, $R^9$ is alkyl, haloalkenyl or haloalkynyl, each of up to 5 carbon atoms, $R^{10}$ is halogen or alkyl of up to 5 carbon atoms, $R^{11}$ is halogen or alkyl of up to 5 carbon atoms, A is halogen, alkyl, alkoxy, trihaloalkyl or trihaloalkoxy, each of up to 5 carbon atoms, cyano or nitro, B is alkyl, alkenyl or alkynyl, each of up to 4 carbon atoms, or an alicyclic radical of 3 to 7 carbon atoms and n is from 0 to 3, $R^2$ is hydrogen, cyano or alkyl, alkenyl or alkynyl, each of up to 5 carbon atoms, and $R^3$, $R^4$, $R^5$, $R^6$ and $R^7$ are identical or different and each is hydrogen, halogen or alkyl, alkenyl, alkynyl or alkoxy, each of up to 5 carbon atoms.

2. A composition for combatting insects, ticks and mites comprising a solid or liquid carrier and an effective amount of at least one substituted 2,3-dihydrobenzofurylmethyl ester of the formula

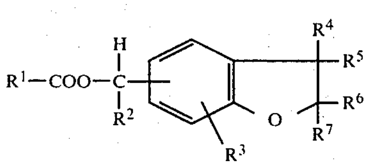

where $R^1$ is 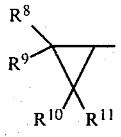 or 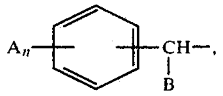

where $R^8$ is hydrogen or alkyl of up to 5 carbon atoms, $R^9$ is alkyl, haloalkenyl or haloalkynyl, each of up to 5 carbon atoms, $R^{10}$ is halogen or alkyl of up to 5 carbon atoms, $R^{11}$ is halogen or alkyl of up to 5 carbon atoms, A is halogen, alkyl, alkoxy, trihaloalkyl or trihaloalkoxy, each of up to 5 carbon atoms, cyano or nitro, B is alkyl, alkenyl or alkynyl, each of up to 4 carbon atoms, or an alicyclic radical of 3 to 7 carbon atoms and n is from 0 to 3, $R^2$ is hydrogen, cyano or alkyl, alkenyl or alkynyl, each of up to 5 carbon atoms, and $R^3$, $R^4$, $R^5$, $R^6$ and $R^7$ are identical or different and each is hydrogen, halogen or alkyl, alkenyl, alkynyl or alkoxy, each of up to 5 carbon atoms.

3. A process for combating insects, ticks and mites, wherein an effective amount of at least one substituted 2,3-dihydrobenzofurylmethyl ester is allowed to act on the pests or their habitat, wherein said ester has the formula

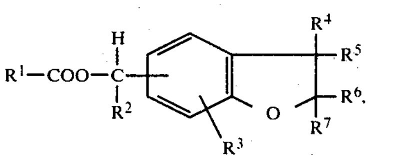

I where $R^1$ is 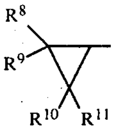 or 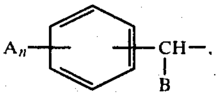

where $R^8$ is hydrogen or alkyl of up to 5 carbon atoms, $R^9$ is alkyl, haloalkenyl or haloalkynyl, each of up to 5 carbon atoms, $R^{10}$ is halogen or alkyl of up to 5 carbon atoms, $R^{11}$ is halogen or alkyl of up to 5 carbon atoms, A is halogen, alkyl, alkoxy, trihaloalkyl or trihaloalkoxy, each of up to 5 carbon atoms, cyano or nitro, B is alkyl, alkenyl or alkynyl, each of up to 4 carbon atoms, or an alicyclic radical of 3 to 7 carbon atoms and n is from 0 to 3, $R^2$ is hydrogen, cyano or alkyl, alkenyl or alkynyl, each of up to 5 carbon atoms, and $R^3$, $R^4$, $R^5$, $R^6$ and $R^7$ are identical or different and each is hydrogen, halogen or alkyl, alkenyl, alkynyl or alkoxy, each of up to 5 carbon atoms.

* * * * *